US009884193B2

(12) United States Patent
Amblard et al.

(10) Patent No.: US 9,884,193 B2
(45) Date of Patent: Feb. 6, 2018

(54) PACEMAKER WITH DETECTION OF ATRIAL ACTIVITY WITHOUT COLLECTION OF ATRIAL ELECTRICAL ACTIVITY

(71) Applicants: SORIN CRM SAS, Clamart (FR); UNIVERSITÉ DE BRETAGNE OCCIDENTALE, Brest (FR); CENTRE HOSPITALIER RÉGIONAL ET UNIVERSITAIRE DE BREST, Brest (FR)

(72) Inventors: Amel Amblard, Sceaux (FR); Jérôme Dumont, Châtillon (FR); Fabrizio Renesto, Borgofranco d'Ivrea (IT); Jacques Mansourati, Brest (FR)

(73) Assignees: SORIN CRM SAS, Clamart (FR); UNIVERSITÉ DE BRETAGNE OCCIDENTALE, Brest (FR); CENTRE HOSPITALIER RÉGIONAL ET UNIVERSITAIRE DE BREST, Brest (FR)

(*) Notice: Subject to any disclaimer, the term of this patent is extended or adjusted under 35 U.S.C. 154(b) by 92 days.

(21) Appl. No.: 14/922,622

(22) Filed: Oct. 26, 2015

(65) Prior Publication Data

US 2016/0114161 A1    Apr. 28, 2016

(30) Foreign Application Priority Data

Oct. 27, 2014    (FR) ..................................... 14 60321

(51) Int. Cl.
*A61N 1/00* (2006.01)
*A61N 1/365* (2006.01)
(Continued)

(52) U.S. Cl.
CPC ............ *A61N 1/365* (2013.01); *A61B 5/6869* (2013.01); *A61N 1/057* (2013.01); *A61N 1/3682* (2013.01);
(Continued)

(58) Field of Classification Search
CPC .. A61N 1/365; A61N 1/37205; A61N 1/3756; A61N 1/36507; A61N 1/3682; A61N 1/3962; A61N 1/057; A61B 5/6869
See application file for complete search history.

(56) References Cited

U.S. PATENT DOCUMENTS

| 2013/0123872 A1 | 5/2013 | Bornzin et al. |
| 2013/0138006 A1 | 5/2013 | Bornzin et al. |
| 2013/0325081 A1 | 12/2013 | Karst et al. |

FOREIGN PATENT DOCUMENTS

| EP | 2 092 885 A1 | 8/2009 |
| EP | 2 189 180 A1 | 5/2010 |

(Continued)

OTHER PUBLICATIONS

Preliminary Search Report for French Patent Application No. 1460321, dated Jun. 16, 2015, 1 page.

*Primary Examiner* — Lindsey G Wehrheim
(74) *Attorney, Agent, or Firm* — Foley & Lardner LLP (57) ABSTRACT

The invention relates to an active implantable pacemaker. The device analyzes a ventricular electrogram signal (EGM) and is able to recognize, in a search window, an EA4 component of endocardial acceleration (EA) associated with atrial activity. In the presence of atrioventricular conduction, the search window is determined based on the temporal position of the EA1 and/or EA2 components of the EA signal. In the absence of atrioventricular conduction, a delay is counted from a paced ventricular event and applied to mask the EA1 and/or EA2 components in the EA signal, and the window for research of the EA4 component follows the (Continued)

masking delay. In the presence of a confirmed EA4 component, an atrioventricular delay is applied, counted from the EA4 component, and in the opposite case a predetermined escape interval is applied, counted from the last stimulated ventricular event.

21 Claims, 7 Drawing Sheets

(51) Int. Cl.
*A61N 1/39* (2006.01)
*A61N 1/05* (2006.01)
*A61B 5/00* (2006.01)
*A61N 1/375* (2006.01)
*A61N 1/368* (2006.01)
*A61N 1/372* (2006.01)

(52) U.S. Cl.
CPC ....... *A61N 1/36507* (2013.01); *A61N 1/3756* (2013.01); *A61N 1/37205* (2013.01); *A61N 1/3962* (2013.01)

(56) References Cited

FOREIGN PATENT DOCUMENTS

| EP | 2 189 182 | 5/2010 |
| EP | 2 311 524 | 4/2011 |
| EP | 2 471 447 | 7/2012 |
| EP | 2 499 971 | 9/2012 |

PACEMAKER WITH DETECTION OF ATRIAL ACTIVITY WITHOUT COLLECTION OF ATRIAL ELECTRICAL ACTIVITY

CROSS-REFERENCE TO RELATED PATENT APPLICATIONS

This application claims the benefit of and priority to French Patent Application No. 1460321, filed Oct. 27, 2014, which is incorporated herein by reference in its entirety.

BACKGROUND

The invention relates to "active implantable medical devices" as defined by the Directive 90/385/EEC of 20 Jun. 1990 of the Council of the European Communities, and particularly implantable devices that continuously monitor the heart rate and if necessary deliver to the heart electrical stimulation, resynchronization and/or defibrillation pulses in case of arrhythmia detected by these devices.

The invention relates especially, but is not limited to, those devices that are in the form of an autonomous capsule intended to be implanted in a heart chamber, including the ventricle.

These capsules are free of any mechanical connection to an implantable (such as a housing of the stimulation pulse generator) or non-implantable (external device such as programmer or monitoring device for patient remote monitoring) main device, and for this reason are called "leadless capsules" to distinguish them from electrodes or sensors disposed at the distal end of a conventional probe (lead), which is traversed throughout its length by one or more conductors galvanically connecting the electrode or sensor to a generator connected to an opposite, proximal end of the lead.

Note, however, that the autonomous nature of the capsule is not inherently a necessary feature of the invention.

The implantation of a leadless capsule in the right or left ventricle allows very simple "single chamber" (stimulation of a single, ventricular, cavity) configuration of a pacemaker. The leadless capsule is provided with a detection/stimulation electrode in contact with the wall of the ventricle, which enables it to detect the presence or absence of a spontaneous ventricular depolarization wave, as well as the occurrence time of this wave (ventricular marker) and, if necessary, to deliver a stimulation pulse in case of missing or late spontaneous depolarization, so as to cause contraction of the ventricle.

However, this mode of operation is limited to a single ventricular chamber stimulation, that is to say in which an escape interval (IE) is programmed to cause stimulation if the time since the last detection or stimulation of the ventricle exceeds the length of this interval, or do nothing in case of detected spontaneous ventricular depolarization.

This mode of operation has the disadvantage that ventricular pacing is not synchronized with the emptying of the atrium, and the pacing rate will not adapt to the sinus rhythm at a given time (sinoatrial rhythm). This can be annoying in case of physical activity because the pace will not accelerate despite increased physiological needs. For adaptation to the rhythm of the patient, there are solutions implementing rate-response servo methods, but they are sub-optimal compared to methods based on the detection of atrial activity, as long as the patient is not chronotropic incompetent.

In the absence of sinus node dysfunction, a VDD mode may be preferred to a single ventricular chamber mode. This VDD mode is obtained by programming a traditional dual chamber pacemaker, but may also be obtained with a single lead device having two atrial "floating" electrodes for atrial detection, and bipolar ventricular stimulation/detection electrodes. However, any atrial pacing is impossible. The detection of atrial activity, that is to say the moment at which the atrium contracts, allows determining the patient's instant sinus rhythm (from successive RR intervals) and thus calculating and applying an atrioventricular delay (AVD) based on that rhythm. Then the pacemaker will operate in VDD mode (ventricular pacing from the signals collected on both the ventricle and atrium).

This method is not possible with a leadless capsule, which by definition has no lead and thus contains no element located in the atrium area.

In such cases, it would be beneficial to detect atrial activity from the leadless capsule implanted in the right or left ventricle, without any opportunity to collect a signal reflecting the electrical activity of the atrium.

The same issue may arise in certain situations with a conventional pacemaker (a device including an endocardial lead connected to a remote generator), for example in case of rupture of an atrial lead, or when the signals delivered using a floating electrode ("floating dipole" configuration) are not of sufficient quality to be able to derive a sufficiently reliable atrial activity signal.

Various proposals have been made to solve the problem of collection of an atrial signal by an endocardial leadless capsule implanted in the right or left ventricle.

US 2013/0325081 A1 describes a leadless capsule in which one of the ends is anchored to the right ventricle and whose opposite free end is provided with an extension having a wire or antenna shape extending into the right atrium. This extension is in contact with the wall of the right atrium and allows the detection/stimulation in the cavity, enabling an operation of the capsule in the DDD or DDDR modes. In another embodiment, the capsule contains no extension, but is provided, at its free end opposite to the anchor point, electrodes for enabling far-field detection of the electrical activity of the right atrium, with application of specific filters or morphological recognition of electrical signals collected at the capsule by these electrodes.

Comparably, US 2013/0138006 A1 uses electrodes on areas of the capsule which are not in contact with the wall of the ventricle, in order to collect far-field electrogram signals. The detection of atrial activity is based on a comparison between the near-field and the far-field, the atrial activity being detected when the far-field signal exceeds a threshold and the near-field signal does not exceed it. This dual atrial/ventricle detection from ventricular electrodes, only based on electrical far-field/near-field signals, remains complex to implement and, in practice, is insufficiently reliable to detect the presence or absence of atrial activity with a high degree of certainty.

EP 2471447 A1 describes a configuration in which a left ventricular stimulation produced by an epicardial capsule is synchronized on a left atrial pacing, also produced by an epicardial capsule. The synchronization is performed by analysis of signals conducted by the heart tissue, the ventricular capsule operating as the slave of the atrial capsule. However, this device involves the presence of an atrial capsule and implanting epicardial capsules in contact with the outer wall of the myocardium, which is a much more complicated procedure than the implantation of a single endocardial capsule.

Yet another proposal is that of US 2013/0123872 A1, wherein a single leadless capsule is used, but placed in the atrium. The problem then is to detect ventricular activity from the atrium, which implies the implementation of complex filters to prevent interference (cross-talk) between atrial and ventricular signals.

None of these devices described above provide a satisfactory solution to the issues described above, because all are based on the collection of electrical information reflecting the activity of the atrium and requiring an atrial electrode.

Pacemakers using a lead with an EA sensor are known, as described for example in EP 2189180 A1 (Sorin CRM S.A.S.). This proposes to adjust the AVD taking as the starting point of the delay the end time of the EA4 wave. The search for EA4 component is performed after detection of a P wave (spontaneous atrial depolarization wave) or after an atrial stimulation A. This configuration requires the availability of a marker of atrial electrical activity (P/A) and it is therefore not applicable to the case of a leadless capsule devoid of collection methods of the electrical activity of the atrium.

Other stimulators using a lead with an EA sensor are described in EP 2499971 A1 (Sorin CRM), which involves an analysis technique of the EA signal to dynamically adjust therapy according to the status of the patient, and in EP 2311524 A1 (Sorin CRM), which involves the concomitant optimization of AVD and VVD based on the results of the analysis of the EA signal.

But neither of these documents relates to the specific problem described above, namely the detection of atrial activity by a device (such as a leadless capsule) implanted in the right or left ventricle, but without an atrial lead or other methods or opportunity to collect a signal reflecting the electrical activity of the atria.

EP 2189182 A1 (Sorin CRM S.A.S) proposes the detection of atrial activity from the EA4 component to confirm atrial capture after stimulation. Detecting the EA4 component is based on energy analysis in sliding windows which validate the presence of a contraction if the energy exceeds a given threshold. For each cardiac cycle, the search window of EA4 component is referenced to the atrial stimulation or detection instant, presupposing as in the previous case the knowledge of a marker of atrial electrical activity (P/A). In any event, to the extent that it is to confirm or not the capture after stimulation of the atrium, the device is necessarily provided with an atrial electrode, the purpose of which is precisely to allow this stimulation of atrium.

None of these documents therefore disclose a method to detect atrial activity without having first a marker of electrical activity to recognize and confirm the existence of atrial contraction.

EP 2092885 A1 (Sorin CRM S.A.S.) describes a processing method of extracting the principal components of an EA signal. This document substantially discloses methods of extracting EA1 and EA2 components corresponding to the two main heart sounds, these methods being possibly transposed to the detection of the EA4 component. The detection of the EA1 and EA2 components requires the definition of predefined search windows based on ventricular electrical markers and depending on the heart rate. However, this does not disclose any method that would define these windows to possibly detect the EA4 component without a marker of atrial electrical activity.

SUMMARY

Various embodiments of the invention detect atrial activity using a signal delivered by an endocardial acceleration (EA) sensor incorporated in a leadless capsule.

Atrial contraction results in an observable specific component in the EA signal, called "EA4 component," the presence or absence of which reveals the existence or not of a contraction of the atria and the moment of its occurrence. Once this component is detected, it becomes possible to trigger an AVD, like a dual chamber pacemaker programmed in VDD would do.

According to an exemplary embodiment, the invention includes a device having a processor configured to:
 detect ventricular events by analysis of a ventricular electrogram EGM signal;
 provide ventricular stimulation;
 apply to the ventricular stimulation an atrioventricular delay AVD, counted from an atrial event and at the end of which a ventricular stimulation is delivered in the absence of detection of a spontaneous ventricular event;
 via an acceleration sensor, deliver an endocardial acceleration EA signal, representative of the cyclic contractions of the myocardium; and
 analyzing the EA signal, the analysis able to recognize and isolate in the EA signal an EA4 component corresponding to the fourth peak of endocardial acceleration associated with atrial activity.

According to an exemplary embodiment, the device is devoid of methods of collection of the atrial EGM signal, and the processor is further configured to:
 determine a search window of the EA4 component in the EA signal;
 prove (e.g. confirm, determine, identify, etc.) the presence or absence of a EA4 component in the search window; and
 apply to the ventricular stimulation:
 the AVD in the presence of a proved EA4 component; or
 a predetermined escape interval in the absence of a proved EA4 component.

Determining the search window may include:
a) in the presence of atrioventricular conduction:
 detecting the moment of occurrence of the ventricular event from the ventricular EGM signal;
 detecting in the EA signal EA1 and/or EA2 components corresponding to the first and/or second respective peaks of endocardial acceleration associated with the ventricular event; and
 determining the search window of the EA4 component depending on the temporal position of detected EA1 and/or EA2 components, and
b) in the absence of atrioventricular conduction:
 applying a masking delay of the EA1 and/or EA2 components in the EA signal, counted from a paced ventricular event; and
 determining the search window of the EA4 component after the masking delay.

According to various advantageous subsidiary characteristics:
 the device is an autonomous intracardiac capsule including a tubular body provided at its distal end with an anchoring member capable of penetrating into a wall of a ventricle of a patient;
 proving the presence or absence of a EA4 component in the search window includes assessing the overall energy level of the signal EA in the search window and comparing the overall energy level to a predetermined threshold;
 proving the presence or absence of a EA4 component in the search window includes morphological analysis of the EA signal in the search window by testing within predetermined windows the passing of local minima and/or local maxima of the EA signal;

the device further estimates the patient's intrinsic rhythm in the absence of atrioventricular conduction, calculated based on the temporal interval between the detection of two proved EA4 components for consecutive cardiac cycles;

in this case, the device further: calculates a ventricular pacing rate as a function of the spontaneous rate value calculated by the estimation; calculates the escape interval as a function of the spontaneous rate value calculated by the estimation; calculates the AVD according to the spontaneous rhythm value calculated by the estimation; and/or calculates the duration of the search window according to the spontaneous rhythm value calculated by the estimation.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the device of the invention will now be described.

Regarding its software aspects, various embodiments of the invention may be implemented by appropriate programming of the controlling software of a known cardiac pacemaker, for example an endocardial leadless capsule.

These devices include a programmable microprocessor provided with circuits for shaping and delivering stimulation pulses to implanted electrodes. It is possible to transmit to it by telemetry software that will be stored in memory and executed to implement the functions of the invention which will be described below. The adaptation of these devices to implement the functions of the invention is within the reach of a skilled-in-the-art person and will not be described in detail. In particular, software stored in memory and executed can be adapted and used to implement the functions of the invention which will be described below.

Various embodiments of the invention are implemented primarily by software, through appropriate algorithms performed by a microcontroller or a digital signal processor. For the sake of clarity, the processing applied will be decomposed and schematized by a number of separate functional blocks in the form of interconnected circuits, but this representation, however, is only illustrative, these circuits including common elements in practice corresponding to a plurality of functions generally performed by the same software.

Figure 1:
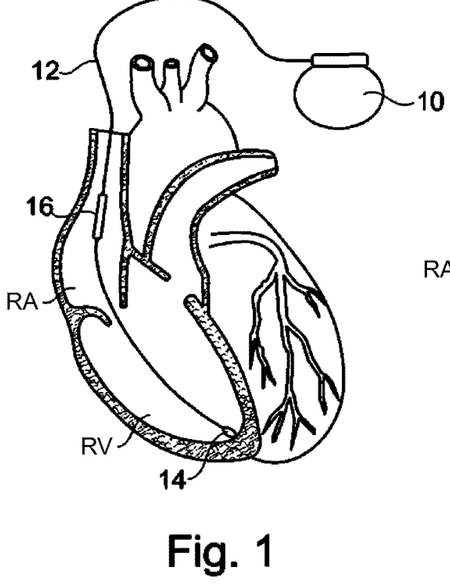
FIG. 1 illustrates a conventional configuration of a single chamber pacemaker, implementing a ventricular endocardial lead connected to generator housing.

In FIG. 1, a conventional configuration of a simple chamber pacemaker is shown, with a generator housing 10 to which an endocardial lead 12 is connected. The endocardial lead 12 is provided at its distal end with a ventricular detection/stimulation electrode 14, typically anchored in the apex of the right ventricle RV to allow detection of a spontaneous depolarization wave of the ventricle, as well as if necessary the stimulation thereof by delivering the pulses produced by the generator 10. The endocardial lead 12 is introduced through the venous system and, to reach the right ventricle, crosses the right atrium RA.

To collect signals reflecting the electrical activity of the atrium, it is possible to provide the body of the lead 12, in the area crossing the atrium RA, with an electrode 16 connected to the generator 10 by an internal conductor of the lead 12, separate from that connected to the ventricular electrode 14. The atrial electrode 16 and the generator 10 then form a "floating" dipole (the electrode 16 is not, or not necessarily, in contact with the wall of the atrium), which collects electrical signals. After filtering and processing, these signals may provide information on the electrical activity of the atria, however with a number of limitations due to the sometimes poor quality of the electrical signal collected by the floating dipole.

Figure 2:
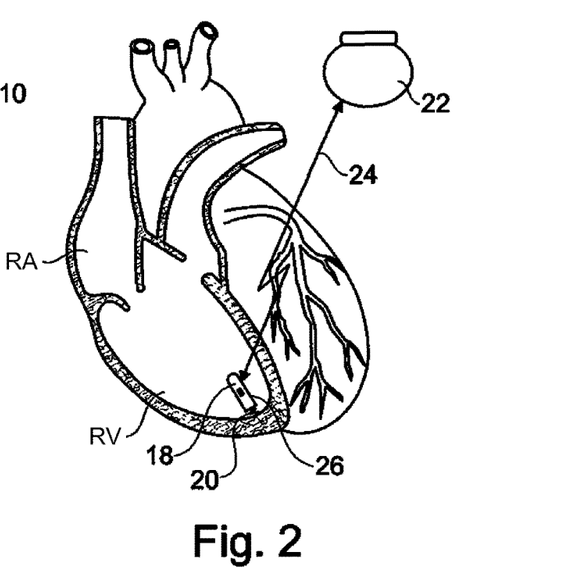
FIG. 2 illustrates a single chamber stimulation configuration implementing a single endocardial leadless capsule implanted in the ventricle, configuration to which the present invention is advantageously applied.

FIG. 2 illustrates a pacemaker configuration implementing a leadless capsule 18 anchored to the bottom of the right ventricle RV, with an electrode 20 in contact with the ventricular wall at this location, this electrode being optionally formed by the anchoring screw of the capsule 18. The capsule 18 is provided with a leadless transmitter/receiver for communicating remotely with an implantable or external housing 22, via a wireless radiofrequency or HBC (Human Body Communication, Communication through intracorporeal) link 24. The housing 22, which acts as a master device, receives the signals collected by the leadless capsule 18, analyzes these signals and optionally sends commands to the capsule 18 so that it delivers stimulation pulses to the ventricle. The housing 22 can also be used as a gateway with the outside world to communicate through RF telemetry with external devices such as programmers or data transmission devices.

It should be noted, however, that the proposed invention is not limited to such a configuration wherein a leadless capsule is interfaced to a master unit (the housing 22). The leadless capsule 18 may indeed be a functionally autonomous capsule, integrating all the collection and analysis circuits of ventricular EGM signal and of communication to external devices.

Typically, the leadless capsule 18 is provided with a sensor 26 of endocardial acceleration (EA), for example in the form of a micro-accelerometer incorporated in the capsule 18, this sensor being capable of delivering a signal representative of the mechanical activity of the myocardium. It is however not essential that the EA sensor is incorporated in the leadless capsule. The invention is also applicable to an analysis made from an EA signal delivered by a separate acceleration sensor, or even by a different type of implantable EA sensor, such as a motion sensor of a wall of the myocardium or an epicardial sensor.

Figure 3:
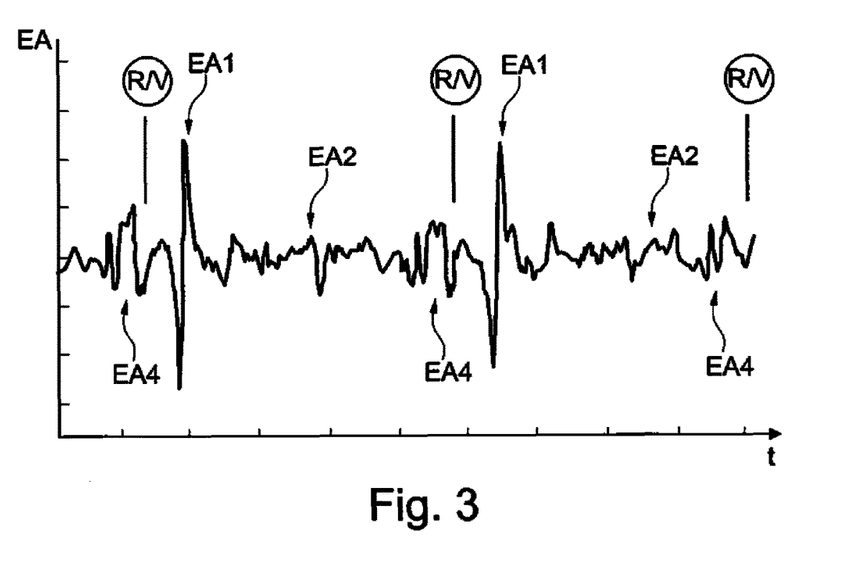
FIG. 3 is a timing diagram illustrating a typical endocardial acceleration signal obtained by an accelerometer sensor integrated to the leadless capsule of FIG. 2.

FIG. 3 illustrates an exemplary endocardial EA signal collected by such a sensor.

On this timing diagram, markers R/V of ventricular electrical activity are reported, obtained by analyzing the signal collected by the electrode 20 (marker R of spontaneous depolarization) or, in the absence of spontaneous depolarization, from the pacing pulse delivered on request by the housing 22 (marker V of stimulated depolarization).

As can be seen in FIG. 3, the EA signal forms over a cardiac cycle a number of components including:

An EA1 component corresponding to the first heart sound (phonocardiogram) and the variations of which are closely related to changes in pressure in the ventricle, the peak amplitude of the EA1 component being more precisely correlated to the positive maximum of the pressure variation dP/dt in the left ventricle;

An EA2 component corresponding to the second cardiac sound during the isovolumetric ventricular relaxation phase produced by the sudden deceleration of the moving blood mass in the aorta; and The other two components of much lower amplitude, called EA3 and EA4, corresponding, in certain conditions, to the S3 and S4 sounds of the phonocardiogram.

The invention relates more particularly to the EA4 component, which is directly linked to the presence of atrial contraction.

This EA4 component has a peak which, as can be seen in FIG. 3, is located immediately before the peak of the EA1 component. For this reason, this component is sometimes referred to as "EA0" by rhythmologists because from the electrical view, the atrial contraction precedes the ventricular contraction. However, if one considers the blood flow pumped by the myocardium, atrial contraction (EA4 component) completes the filling of the ventricles at the end of diastole (EA2 component) and therefore falls, from cardiac hemodynamics viewpoint, after the latter, hence the term "EA4" component.

One problem addressed by the invention as described herein, is to obtain information on atrial activity only from this EA signal and a R/V ventricular electrical activity marker, in order to ensure VDD operating mode as soon as possible.

Figure 4:
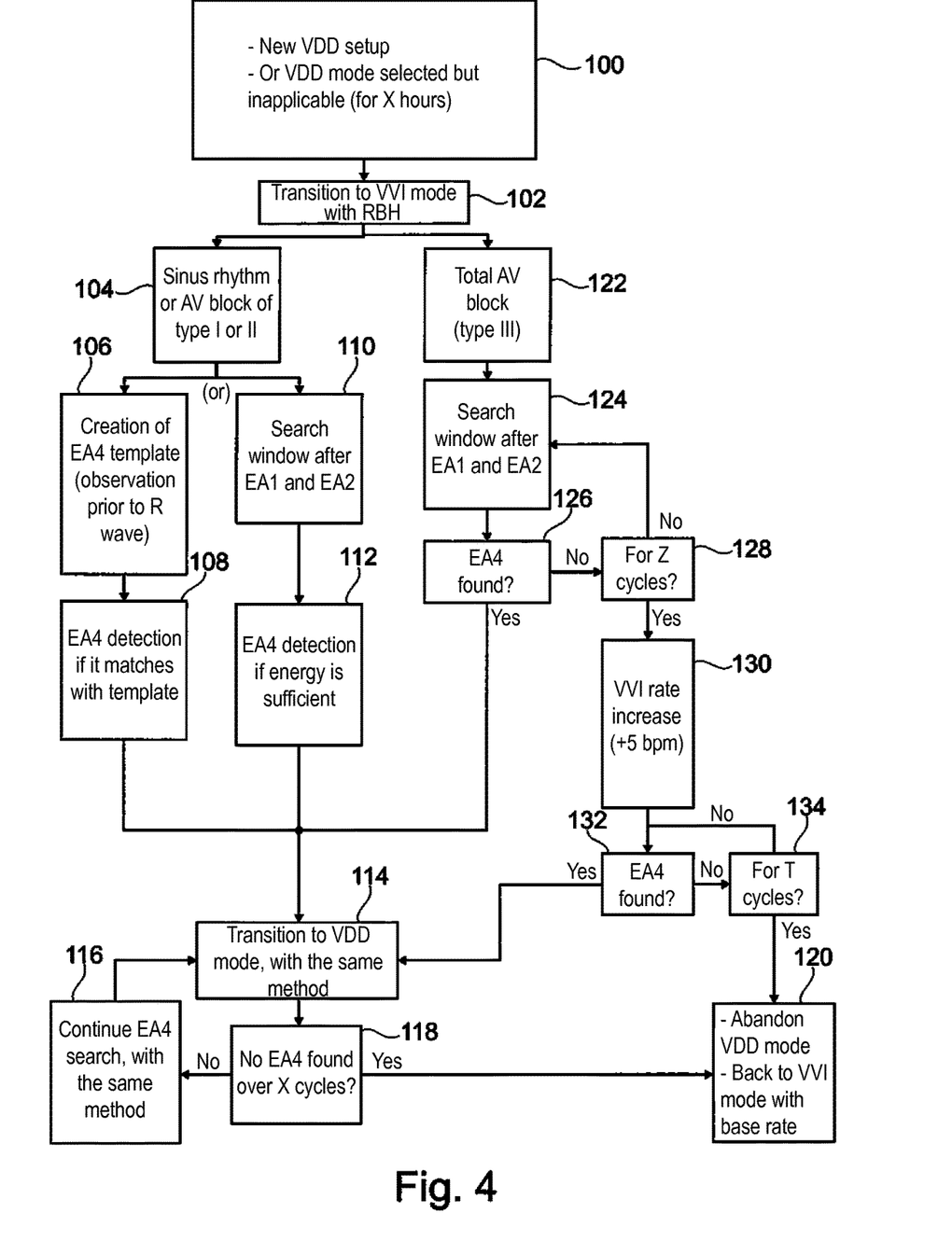
FIG. 4 is a block diagram illustrating the main steps of the method of the invention, in particular the selection of the research method of atrial contraction depending on the presence or absence of full atrioventricular (AV) block.

First, as shown in FIG. 4, two clinical cases must be distinguished, depending on whether or not the patient has full atrioventricular block (AV block).

For this purpose, the capsule 18 is designed to be able to select two different programmed basic rhythms, namely:

A standard base rate, BR hereinafter, which will be applied when operating in the VVI mode (that is to say in the event of impossible synchronization with the atria), typically BR=70 bpm; or A hysteresis base rate, HBR hereinafter, which is lower than BR (or equal to BR if the practitioner prefers to disable this functionality), typically HBR=50 bpm. This reduced base rhythm corresponds to the lowest permitted spontaneous rhythm when synchronization with the atria is possible, and aims to promote resynchronization with the atrium even if the patient's intrinsic rhythm is quite low.

The method begins (block 100) on a scheduling request of VDD mode, or every X hours (e.g. X=1 or 2 hours) when the VDD mode is selected but could not be applied.

The unit will remain in VVI mode but temporarily switches to the HBR frequency (block 102).

The next step (block 104) is to detect the presence or not of a spontaneous rhythm by search of recurring R waves.

If a spontaneous rhythm is observed, the situation corresponds to sinus rhythm or partial AV block (block of type I or II) which does not completely prevent conduction between the atrium and ventricle (block 104).

Figure 5:
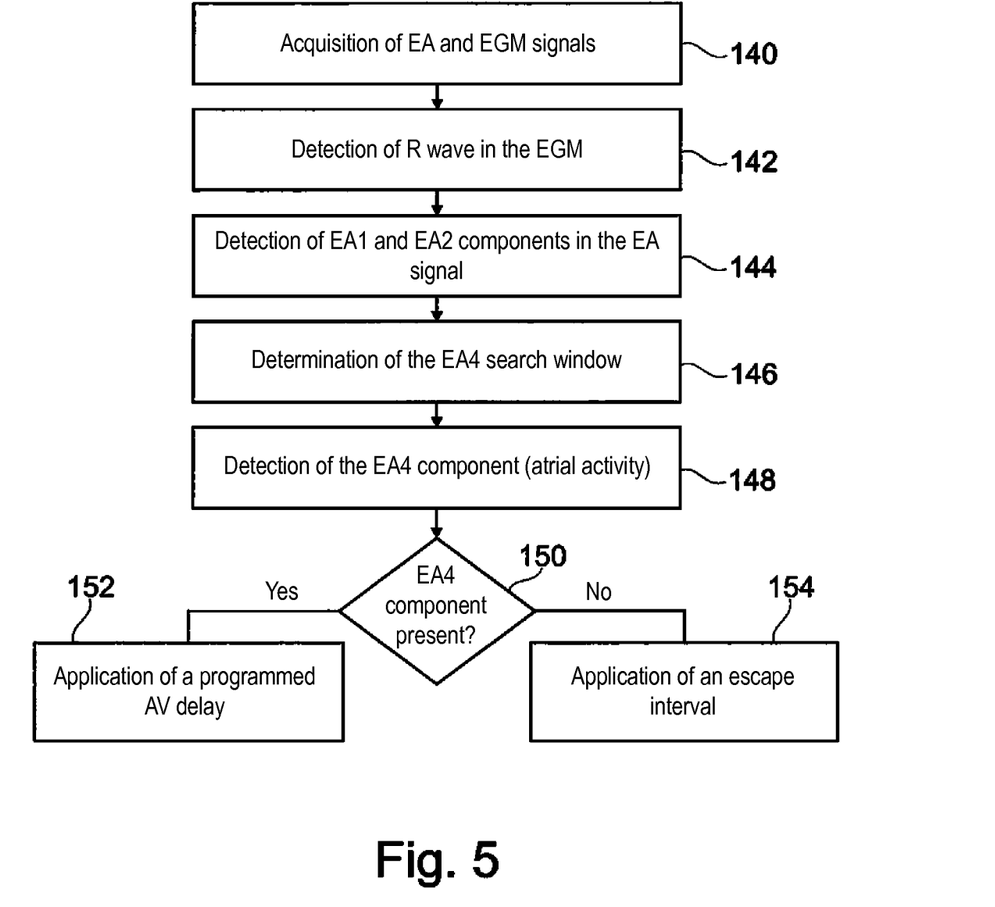
FIG. 5 is a flow chart outlining the main steps of the method of the invention, as implemented in the absence of complete AV block.

Detection of atrial activity is then made according to a first method, described with reference to FIGS. 5 to 7, wherein the EA4 component may be detected either by comparison with a template (blocks 106, 108), or by searching energy in a window positioned after EA1 and EA2 waves (blocks 110, 112), which exist, since in this situation the ventricle contracts.

The apparatus then operates in standard VDD mode (block 114), with application of an AVD on detection of the EA4 components, and application of an escape interval EI in case of absence of detection of the EA4 component, typically in the case of sinus bradycardia or of atrial rapid tachycardia (flutter or atrial fibrillation). In case of the absence of detection of the EA4 component (block 116) over a predetermined number Y of cycles, typically 20 cycles (block 118), then the VDD mode is abandoned to return to VVI mode with standard base rhythm BR (block 120).

If the VVI mode with reduced base rate RBH (block 102) shows no spontaneous ventricular activity, then a complete AV block is likely (block of type III), that is to say a deficient atrioventricular conduction wherein the depolarization of the atria is not transmitted to the ventricles, which will not contract spontaneously (block 122).

Insofar as a marker of the ventricular electrical activity is no longer available, another, more complex method, of search of the EA4 component must be used. Such a method is described with reference to FIGS. 8 to 11. An EA4 wave is then expected in a detection window set after the EA1 and EA2 components (block 124). Once an EA4 component is found (block 126), then the device returns to VDD (block 114, described above). In case of non-detection of the EA4 component over a predetermined number Z of cycles, typically the last 20 cycles (block 128), then the device slightly increases the pacing rate, e.g. +5 bpm (block 130). Indeed, it is possible that the reduced base rate RBH is very close to the patient's rhythm and then the EA2 component never falls in its search window. After this change of pace, if no EA4 component is found (block 132) after a predetermined number of cycles T, typically 20 cycles (block 134), then the VDD mode is abandoned to return to VVI mode with standard rate base RB (block 120, described above).

Case of Patients in Sinus Rhythm or with Partial AV Block (of Type I or II)

Firstly, a technique of detection of the EA4 component applicable to patients with only a partial branch block (type I or II) will be described with reference to FIGS. 5-7.

In such a case, the atrioventricular conduction is preserved and it is possible to detect an R-wave and to derive from it a ventricular electrical activity marker. Besides, the ventricle contracting, the EA signal will include EA1 and EA2 components related to mechanical activity of the ventricles.

Once the EA acceleration and electrical EGM signals are acquired (step 140), the R wave is detected in the EGM signal (step 142) according to a conventional method. In the EA signal, the EA1 and EA2 components are detected (step 144) in order to then define a search window of the EA4 component (step 146), positioned after the EA2 component.

The device then searches for an EA component in the window thus defined (step 148):

If an EA4 component is present (block 150), this reveals the presence of effective atrial activity, and it is then possible to apply an atrioventricular delay (AVD) with preprogrammed value (block 152), counted from the atrial activity marker defined by the temporal position of the detected EA4 component. The device then operates in the VDD mode;

In the absence of EA4 component in the search window, it can be assumed that there was no contraction of the atrium. In this case, the device applies a predetermined escape interval (EI) (block 154), that is to say an interval, measured from the last ventricular marker, at the expiration of which ventricular pacing is automatically triggered (operation corresponding to a VVI mode).

In the case wherein an AVD is applied, it can be established according to different methods:

A predetermined fixed value;

A plurality of predetermined fixed values, for example a value different of the value at exercise and at rest, these values being selected according to the patient's current physical activity status;

A dynamically adjusted value based on the patient's heart rate (this rate being determined from intervals between successive detected R markers); and/or A periodically optimized value based on indicators of the clinical status of the patient, calculated from a history of endocardial acceleration data collected over a given period of time and to assess the evolution of the patient's hemodynamic status.

Two possible methods for detection of the presence of an EA4 component in the search window will now be described with reference to FIGS. 6 and 7.

Figure 6:
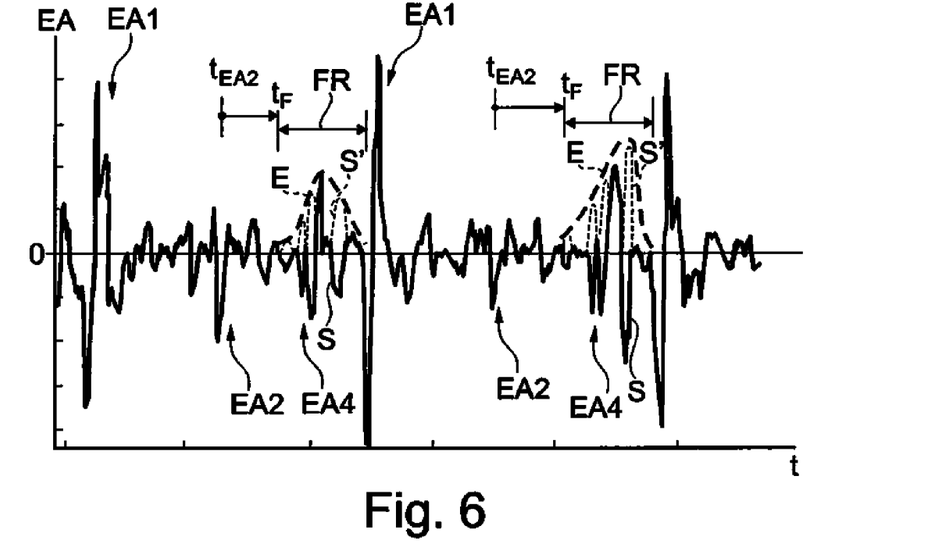
FIGS. 6 and 7 are timing diagrams illustrating two possible respective methods, in the absence of complete AV block, for detecting the EA4 component in the collected EA signal.

With the first technique, illustrated in FIG. 6 and corresponding to blocks 110 and 112 of FIG. 4, the device first detects the EA2 component for defining the temporal position of the search window of the EA4 component. The EA2 component can be detected and characterized by various known methods such as those described in EP 2092885 A1 (Sorin CRM) above. The analysis of the EA signal allows for defining the moment of occurrence $t_{EA2}$ of the EA2 component, or alternatively, an instant corresponding to the end of this component.

Alternatively, in case of difficulty in detecting the EA2 component, another method is to define the position of the search window based on the EA1 component or the instant of detection of the T wave.

Once the EA2 component is detected, the device calculates an instant $t_F$ of opening of a search window FR, the beginning of this window FR being calculated from the instant of occurrence (or end) of the EA2 component, an instant to which a fixed delay or a delay function of the instantaneous heart rate (as determined by the duration of successive RR intervals) is added.

In the search window FR, the signal S is rectified (signal S') and squared so as to define an energy envelope E of the rectified EA signal for the duration of the window FR. After integration, one obtains a total value of the energy of the EA4 component of the signal, and this value is compared to a predetermined threshold. If the threshold is exceeded, it is considered that an EA4 component is actually present, and vice versa if the energy level is below the threshold, it is considered that the EA4 component was not detected or could not be detected.

Figure 7:
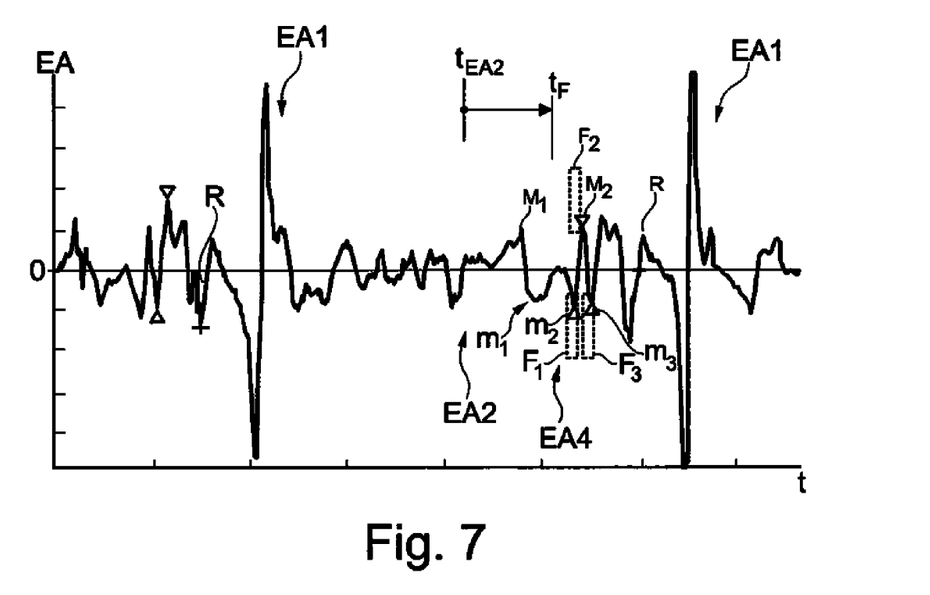

FIG. 7 illustrates another technique of detection of the EA4 component, based on morphological analysis and corresponding to the blocks 106 and 108 of FIG. 4. This technique is particularly suited to the strongly marked pseudo-periodic character of the EA4 component.

After having, as in the previous case, a determined a temporal marker $t_{EA2}$ related to the detection of the EA2 component and defined a start instant $t_F$ of a search window from this $t_{EA2}$ marker, the EA signal is analyzed to search for the local maxima $M_i$ and local minima $m_i$ located in the search window, that is to say posterior to the instant $t_F$.

The detection of the EA4 component consists in determining whether these local minima and maxima are within predetermined windows $F_1, F_2, F_3 \ldots$ for applying Boolean criteria for deciding the detection or not of an EA4 component. If, e.g. two of the three local extrema subsequent to the beginning of the search window are within the predetermined window, then it is considered that an EA4 component is detected.

Thus, in the example of FIG. 7 extrema $M_1$ and $m_1$ are not considered because they are before the beginning of the search window. However, the following extrema $m_2$, $M_2$ and $m_3$ are taken into account, and as they all fit in the three respective predetermined windows $F_1$, $F_2$, $F_3$, then it is possible to confirm the detection of an EA4 component.

It is necessary to provide a preliminary learning phase to define the position of analysis windows $F_1, F_2, F_3 \ldots$. This learning can be performed as follows:

For a predetermined number of beats, for example 30 beats, the instant of the ventricular depolarization (R marker) is determined, which serves as a reference for the opening of a retrospective window;

All local maxima and minima of the EA signal located in this retrospective window are then detected;

On the averaged EA signal, the first, e.g. three or four local extrema are detected in the search window (the first local extrema are chosen rather than the others, because of their relative stability from one cardiac beat to the other);

From the respective local extrema sets thus recorded, the temporal position and the amplitude of each window is determined that will characterize the relative positions and typical amplitudes of the EA4 component.

Case of Patients with Total AV Block (of Type III)

A detection technique of the EA4 component applicable to patients with a total AV block (AV block of type III) will now be described, with reference to FIGS. 8-11.

Figure 8:
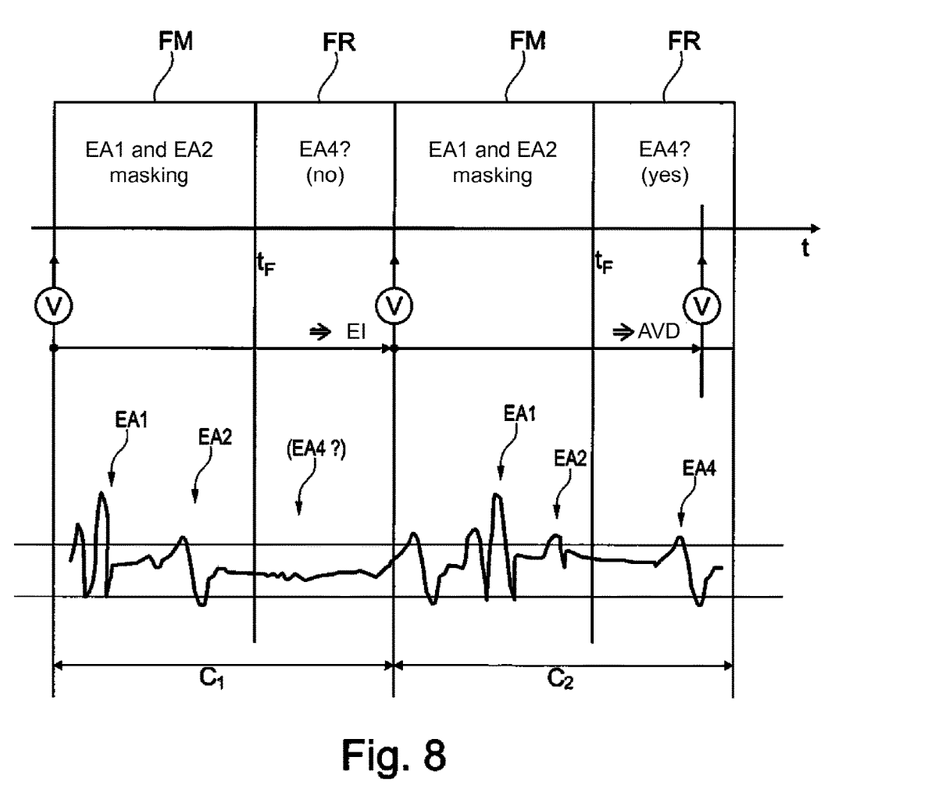
FIG. 8 schematically shows one principle of a method according to the invention, as implemented in the presence of a complete AV block.

In such a situation, atrioventricular conduction is absent and the ventricle, which does not spontaneously contract, must be stimulated.

As shown in FIG. 8, it is necessary to define an FM masking window to ignore the EA1 and EA2 components. The FM masking window is initiated on the ventricular pacing marker V.

The detection of the EA4 component is then launched, in a search window FR open from an instant $t_F$. It will be appreciated that in practice the atrial contraction may be present but occurring more or less concomitantly with the contraction (stimulated) of the ventricle, so it can happen that the EA4 component is superimposed in fact to the EA1 or EA2 components and that, although present, it is not detected in the search window.

According to whether an EA4 component is or is not detected in the search window FR, the action to take is different:

In the absence of detected EA4 component (illustrated by the case of the cycle C1), the device initiates a ventricular stimulation after an escape interval EI;

If an EA4 component is detected (illustrated by the case of the cycle C2), meaning that the atrial contraction is actually present, that it can be located in time and that it is not concomitant with the stimulated contraction of the ventricle, then an AVD can be applied, counted from the instant of occurrence (or, alternatively, the end) of the detected EA4 component.

Figure 9:
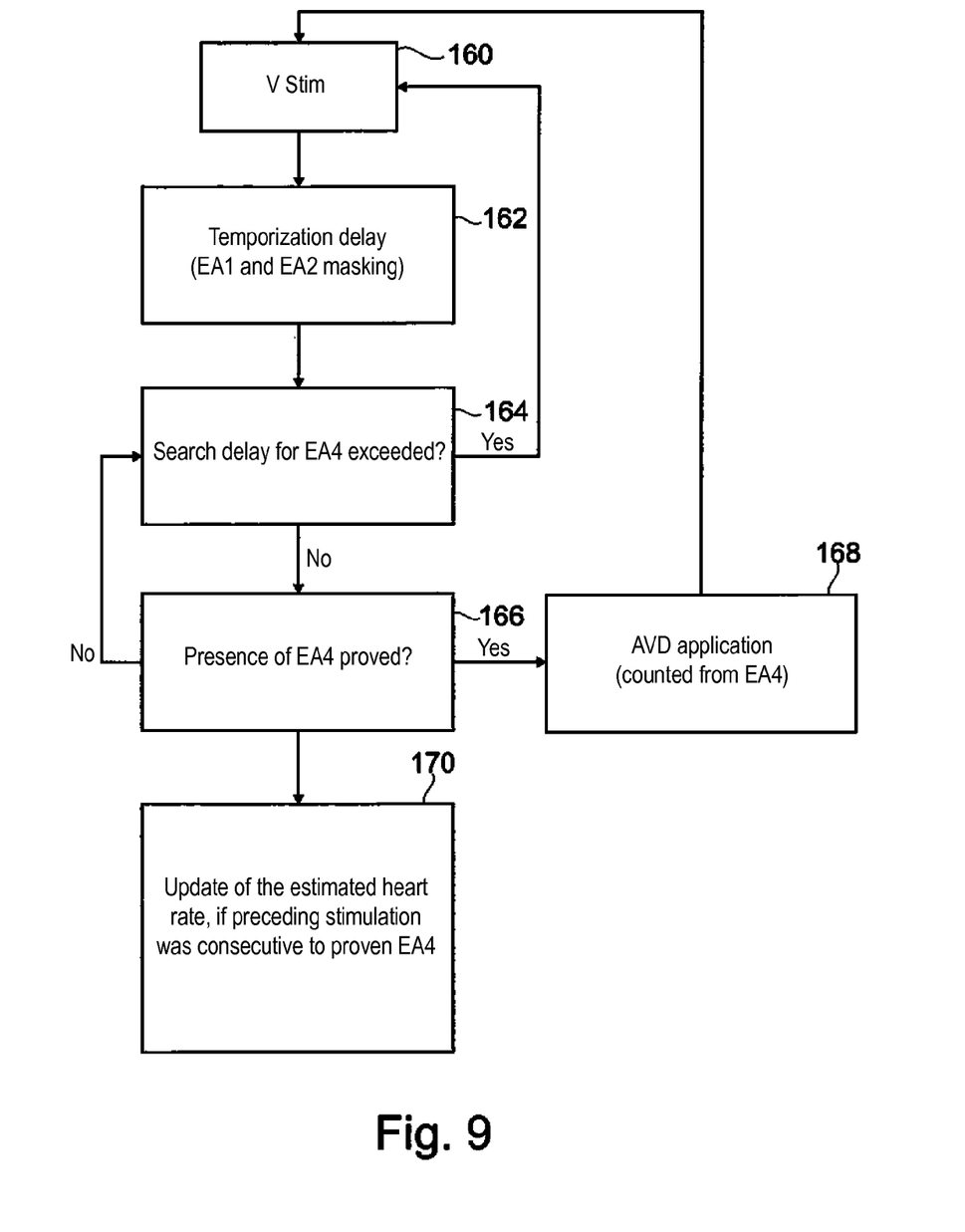
FIG. 9 is a flow chart outlining the main steps of one method according to the invention, as implemented in the presence of a complete AV block.

FIG. 9 is a flowchart summarizing the operating mode applied by the method of the invention, in this case of total AV block.

After stimulation of the ventricle (step 160) a temporization period is counted (step 162) so as to mask on the EA signal the EA1 and EA2 components consecutive to the contraction of the ventricle.

After expiration of this temporization period (corresponding to the mask window FM of FIG. 8), the EA signal is analyzed to detect the presence of an EA4 component during the duration of the search window FR (step 164).

The presence of an EA4 component in the search window FR can be implemented using techniques such as those described above with reference to FIGS. 6 and 7, namely by:

Determination of the energy of the EA signal in a predetermined window, and thresholding; and/or Comparison of the signal with a template, for example with the local extrema of the EA signal falling within predetermined windows.

At the end of the search window FR, the device determines the presence or not of an EA4 component (step 166):

If so, an AVD is applied (step 168), counted from the detection of the EA4 component, which in this case replaces the atrial electrical marker used by devices implementing a detection electrode in the atrium;

In the negative, at the end of the window FR (step 170) a stimulation is always issued after an escape interval EI.

In the case wherein an AVD is applied, this one may be:

A predetermined fixed value;

A plurality of predetermined fixed values, for example a different value for the exercise and rest, of these values being selected according to the patient's current physical activity status;

A dynamically adjusted value based on the patient's heart rate (this rate being determined from intervals between successive detected R markers); and/or A periodically optimized value based on indicators of the clinical status of the patient, calculated from a history of endocardial acceleration data collected over time and to assess the evolution of the patient's hemodynamic status.

In the case wherein an EI is applied, the length of this EI (that is to say the pacing rate in VVI mode) is advantageously determined from an estimate of the patient's spontaneous rate, for example 80% of the estimated rate. This spontaneous rhythm is estimated from a number of successive heartbeats, after averaging of intervals between successive EA4 components. The calculation of this EI therefore requires the detection of EA4 components of several consecutive cycles to estimate the interval, for example over eight cycles. If there are not eight consecutive cycles with detection of the EA4 component, then the escape interval defined by the reduced base rate RBH is applied (see above description with reference to FIG. 4).

Figure 10:
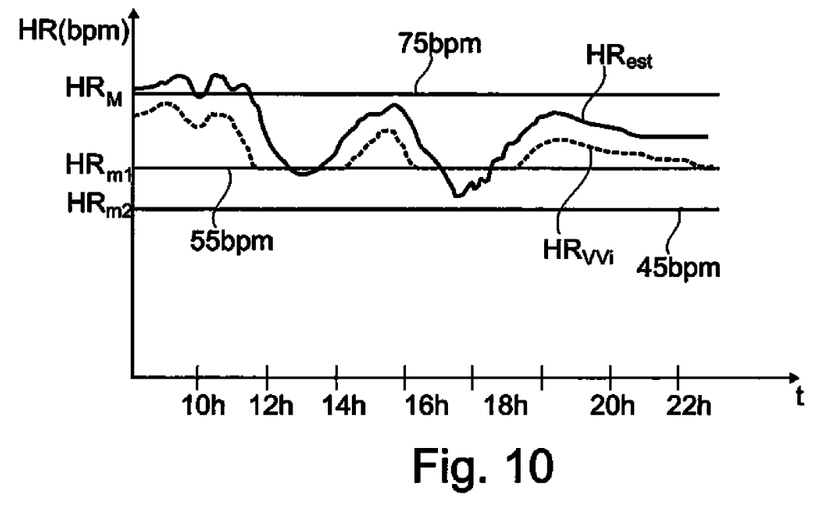
FIG. 10 is a timing diagram illustrating one method by which the escape interval is calculated and bounded in the presence of a complete AV block.

FIG. 10 illustrates in $HR_{est}$ such an exemplary estimated heart rate. This estimate is bounded by:

A maximum value defined by the shortest interval allowing satisfactory pursuit of the EA4 component, e.g. with a masking window FM of 600 ms followed by a search window FR of 200 ms (minimum duration of this window). This gives a duration of 600+200=800 ms, corresponding to a maximum heart rate HRM equal to 75 bpm, and A minimum value defining the rate in standard VVI pacing mode, for example with a $HR_{m1}$ value during the day of 55 bpm and a $HR_{m2}$ overnight of 45 bpm. This rate is the reduced base rate RBH described above with reference to FIG. 4, which may optionally assume two different values, one for the day and one at night.

This produces an estimated value $HR'_{est}$ of the heart rate, from which the heart rate to be applied $HR_{VVI}$ (e.g. $HR_{VVI}=80\% \times HR'_{est}$ and $HR_{VVI} \geq HR_{min}$) is calculated, which defines a corresponding value of the escape interval EI.

Figure 11:
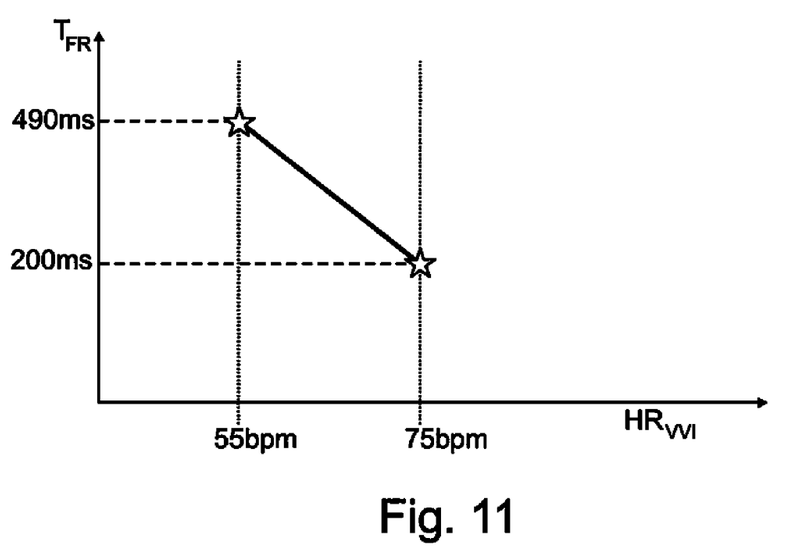
FIG. 11 is a characteristic showing the variation of the position of the search window of the EA4 component based on the calculated duration of the escape interval, in the presence of a complete AV block.

FIG. 11 illustrates how the duration $T_{FR}$ of the search window FR is adapted according to the heart rate HR.

The heart rate value used, $HR_{VVI}$, corresponds to the escape interval, determined as explained above from the spontaneous rhythm and increased or decreased according to the specified rules.

The duration of the search window $T_{FR}$ varies for example linearly with the pace $HR_{VVI}$, between a maximum duration of 490 ms for a heart rate (minimum) of 55 bpm and a minimum duration of 200 ms for a heart rate (maximum) of 75 bpm.

What is claimed is:

1. An active implantable medical device, such as a cardiac pacemaker, for stimulation, resynchronization and/or defibrillation, comprising:
    an acceleration sensor adapted to deliver an endocardial acceleration (EA) signal, representative of cyclic contractions of a myocardium;
    at least one electrode;
    a pulse generator; and
    a processor configured to:
        analyze a ventricular electrogram (EGM) signal obtained using the at least one electrode to detect a plurality of cardiac events;
        trigger ventricular stimulation via the at least one electrode and the pulse generator;
        apply an atrioventricular delay (AVD); and
        analyze the EA signal, wherein the analysis comprises recognizing and isolating in the EA signal an EA4 component corresponding to a fourth peak of an endocardial acceleration associated with an atrial activity, wherein the device does not collect an atrial EGM signal and wherein the processor is further configured to:
        determine a search window for the EA4 component in the EA signal;
        confirm the presence or absence of the EA4 component in the search window; and
        apply stimulation including:
            the AVD in the presence of a confirmed EA4 component; or
            a predetermined escape interval in the absence of a confirmed EA4 component,
        wherein the determination of the search window comprises:
            analyzing the ventricular EGM to determine a presence or an absence of an atrioventricular conduction; and
            a) in the presence of the atrioventricular conduction:
                detecting a time of occurrence of a ventricular event from the ventricular EGM signal;
                detecting in the EA signal an EA1 component and/or an EA2 component corresponding to a respective first peak and/or a second peak of endocardial acceleration associated with the ventricular event; and determining the search window for the EA4 component depending on a temporal position of the detected EA1 and/or EA2 components, and b) in the absence of the atrioventricular conduction:

applying a masking delay, determined by the analysis of the EA signal, of the EA1 and/or the EA2 components in the EA signal, where the delay begins at the EA1 component and ends after the EA2 component; and setting the search window of the EA4 component for after the masking delay has ended.

2. The device of claim 1, wherein the device is an intracardiac autonomous capsule comprising a tubular body provided at a distal end with an anchoring member capable of penetrating into a wall of a ventricle of a patient.

3. The device of claim 1, wherein confirming the presence or absence of the EA4 component in the search window comprises assessing an overall energy level of the EA signal in the search window and comparing the overall energy level to a predetermined threshold.

4. The device of claim 1, wherein confirming the presence or absence of the EA4 component in the search window comprises providing a morphological analysis of the EA signal, the morphological analysis comprising determining if the EA4 component is within a predetermined window of a local minima and/or a local maxima of the EA signal.

5. The device of claim 1, wherein the processor is further configured to estimate an intrinsic rhythm of the patient in the absence of atrioventricular conduction, calculated based on a time interval separating a detection of two confirmed EA4 components for consecutive cardiac cycles.

6. The device of claim 5, wherein the processor is further configured to calculate a ventricular pacing rate depending on a value of spontaneous rhythm calculated by an estimation of the intrinsic rhythm of the patient.

7. The device of claim 5, wherein the processor is further configured to calculate an escape interval according to the value of spontaneous rhythm calculated by the estimation of the intrinsic rhythm of the patient.

8. The device of claim 5, wherein the processor is further configured to calculate the AVD in accordance with the value of spontaneous rhythm calculated by the estimation of the intrinsic rhythm of the patient.

9. The device of claim 5, wherein the processor is further configured to calculate a duration of the search window based on the value of spontaneous rhythm calculated by the estimation of the intrinsic rhythm of the patient.

10. The device of claim 1, wherein the at least one electrode comprises a stimulation electrode configured to trigger ventricular stimulation.

11. The device of claim 1, wherein the at least one electrode comprises a detection electrode configured to obtain the ventricular EGM signal.

12. An active implantable medical device, comprising:
an acceleration sensor adapted to deliver an endocardial acceleration (EA) signal, representative of cyclic contractions of a myocardium;
at least one electrode;
a pulse generator; and
a processor configured to:
analyze a ventricular electrogram (EGM) signal obtained using the at least one electrode to detect a plurality of cardiac events;
trigger ventricular stimulation via the at least one electrode and the pulse generator;
apply an atrioventricular delay (AVD);
analyze the EA signal, wherein the analysis comprises recognizing and isolating in the EA signal an EA4 component corresponding to a fourth peak of an endocardial acceleration associated with an atrial activity, and wherein the processor is further configured to:
determine a search window for the EA4 component in the EA signal;
confirm the presence or absence of the EA4 component in the search window; and
apply stimulation including:
the AVD in the presence of a confirmed EA4 component; or
a predetermined escape interval in the absence of a confirmed EA4 component.

13. The device of claim 12, wherein the at least one electrode comprises a stimulation electrode configured to trigger ventricular stimulation.

14. The device of claim 12, wherein the at least one electrode comprises a detection electrode configured to obtain the ventricular EGM signal.

15. The device of claim 12, wherein the processor is further configured to analyze the ventricular EGM signal to determine a presence or an absence of atrioventricular conduction.

16. The device of claim 14, wherein in the presence of atrioventricular conduction, the processor is further configured to determine the search window for the EA4 component by:
detecting a time of occurrence of a ventricular event from the ventricular EGM signal;
detecting in the EA signal an EA1 and/or an EA2 components corresponding to a respective first and/or a second peaks of endocardial acceleration associated with the ventricular event; and
determining the search window for the EA4 component depending on a temporal position of the EA1 and/or the EA2 components.

17. The device of claim 14, wherein in the absence of atrioventricular conduction, the processor is further configured to determine the search window for the EA4 component by:
applying a masking delay, determined by the analysis of the EA signal, of the EA1 and/or the EA2 components in the EA signal, where the delay beings at the EA1 component and ends after the EA2 component; and
setting the search window of the EA4 component for after the masking delay has ended.

18. The device of claim 14, wherein the device is an intracardiac autonomous capsule comprising a tubular body provided at a distal end with an anchoring member capable of penetrating into a wall of a ventricle of a patient.

19. The device of claim 14, wherein confirming the presence or absence of the EA4 component in the search window comprises assessing an overall energy level of the EA signal in the search window and comparing the overall energy level to a predetermined threshold.

20. The device of claim 14, wherein confirming the presence or absence of the EA4 component in the search window comprises providing a morphological analysis of the EA signal, the morphological analysis comprising determining if the EA4 component is within a predetermined window of a local minima and/or a local maxima of the EA signal.

21. A method comprising:
- delivering, by an acceleration sensor, an endocardial acceleration (EA) signal representative of cyclic contractions of a myocardium;
- obtaining, by one or more electrodes, a ventricular electrogram (EGM) signal;
- triggering, by the one or more electrodes and a pulse generator, ventricular stimulation;
- applying an atrioventricular delay (AVD); and
- analyzing the EA signal, wherein the analysis comprises recognizing and isolating in the EA signal an EA4 component corresponding to a fourth peak of an endocardial acceleration associated with an atrial activity, wherein the recognizing and isolating of the EA4 component comprises:
  - determining a search window for the EA4 component in the EA signal, wherein the determination of the search window comprises;
    - analyzing the ventricular EGM to determine a presence or an absence of atrioventricular conduction; and
    - a) in the presence of the atrioventricular conduction:
      - detecting a time of occurrence of a ventricular event from the ventricular EGM signal;
      - detecting in the EA signal an EA1 component and/or an EA2 component corresponding to a respective first peak and/or a second peak of endocardial acceleration associated with the ventricular event; and
      - determining the search window for the EA4 component depending on a temporal position of the detected EA1 and/or EA2 components, or
    - b) in the absence of the atrioventricular conduction:
      - applying a masking delaying, determined by the analysis of the EA signal, of the EA1 and/or the EA2 components in the EA signal, where the delay begins at the EA1 component and ends after the EA2 component; and
      - setting the search window of the EA4 component for after the masking delay has ended,
  - confirming the presence or absence of the EA4 component in the search window; and
  - applying to the ventricular stimulation:
    - the AVD in the presence of a confirmed EA4 component; or
    - a predetermined escape interval in the absence of a confirmed EA4 component.

* * * * *